(12) United States Patent
Fu et al.

(10) Patent No.: US 8,057,409 B2
(45) Date of Patent: Nov. 15, 2011

(54) ULTRASONIC THERAPEUTIC DEVICE AND AN ULTRASONIC THERAPEUTIC SYSTEM OF USING THE SAME

(75) Inventors: Bing Fu, Chongqing (CN); Youxiang Peng, Chongqing (CN); Yue Gu, Chongqing (CN); Long Wang, Chongqing (CN); Hai Wang, Chongqing (CN)

(73) Assignee: Chongqing Ronghai Medical Ultrasound Industry Ltd., Chongqing (CN)

( * ) Notice: Subject to any disclaimer, the term of this patent is extended or adjusted under 35 U.S.C. 154(b) by 274 days.

(21) Appl. No.: 12/376,472

(22) PCT Filed: Feb. 14, 2007

(86) PCT No.: PCT/CN2007/000544
§ 371 (c)(1),
(2), (4) Date: Feb. 5, 2009

(87) PCT Pub. No.: WO2008/025191
PCT Pub. Date: Mar. 6, 2008

(65) Prior Publication Data
US 2010/0234773 A1 Sep. 16, 2010

(30) Foreign Application Priority Data
Aug. 24, 2006 (CN) .......................... 2006 1 0111925

(51) Int. Cl.
*A61N 7/00* (2006.01)
*A61B 5/055* (2006.01)

(52) U.S. Cl. ................ 601/2; 601/3; 600/411; 600/427; 600/439

(58) Field of Classification Search .................. 600/437, 600/443, 444, 445, 459, 411, 427, 439; 601/3, 601/2, 4; 73/633, 644
See application file for complete search history.

(56) References Cited

U.S. PATENT DOCUMENTS

| 6,533,738 B1 * | 3/2003 | Bauer et al. .................. 601/4 |
| 6,626,855 B1 | 9/2003 | Weng et al. |
| 6,778,848 B1 | 8/2004 | Bechtold et al. |
| 2005/0015024 A1 | 1/2005 | Babaev |

FOREIGN PATENT DOCUMENTS

| CN | 1743026 A | 3/2006 |
| CN | 1814324 A | 8/2006 |

* cited by examiner

*Primary Examiner* — Ruth S Smith
*Assistant Examiner* — Phong K Huynh
(74) *Attorney, Agent, or Firm* — The Webb Law Firm (57) ABSTRACT

An ultrasonic therapeutic device and an ultrasonic therapeutic system including the ultrasonic therapeutic device and guided by an imaging device are provided. The ultrasonic therapeutic device includes an ultrasonic therapeutic applicator that comprises an ultrasonic transducer, a box which contains the ultrasonic therapeutic applicator and the couplant liquid, a moving unit which extends through the wall of the box and connects the ultrasonic therapeutic applicator, and compensating units which set on opposing sides of and incorporate with the box and holds the level of the liquid when the moving unit drives the ultrasonic therapeutic applicator to move. Stabilization of the liquid level in the box consequently decreases the interference to imaging results of an imaging device due to the level changing of the couplant liquid and improves the diagnostic accuracy of the imaging device.

8 Claims, 6 Drawing Sheets

ULTRASONIC THERAPEUTIC DEVICE AND AN ULTRASONIC THERAPEUTIC SYSTEM OF USING THE SAME

FIELD OF THE INVENTION

The present invention pertains to the field of ultrasonic therapy, and particularly relates to an ultrasonic therapeutic device and an ultrasonic therapeutic system guided by an imaging device of using the same.

BACKGROUND OF THE INVENTION

The therapeutic principle of a focused ultrasonic therapeutic system is to employ ultrasonic waves that are capable of going through the physical tissue and being focused within the tissue. Therefore, the ultrasonic beams are focused accurately at the diseased part of a patient and the instantaneous high temperature caused by focusing at a focal spot can cause coagulation necrosis of tissue within the targeted location, and the non-invasive therapy can be achieved. The imaging device such as MRI can quickly obtain the images of the internal body structures of a patient with high accuracy; therefore, the imaging device is always used together with an ultrasonic therapeutic system.

Figure 1:
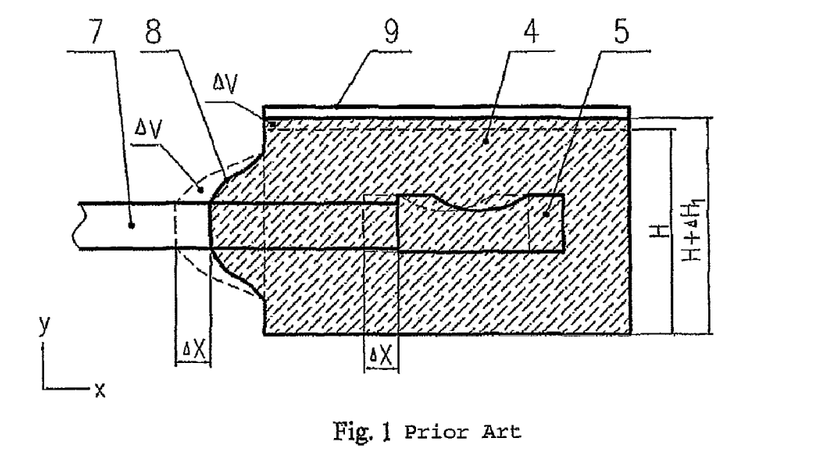
FIG. 1 is a structural diagram of an ultrasonic therapeutic device of prior art. It shows the level changes of couplant liquid when the moving unit drives the ultrasonic therapeutic applicator to move in X-direction.
Figure 2:
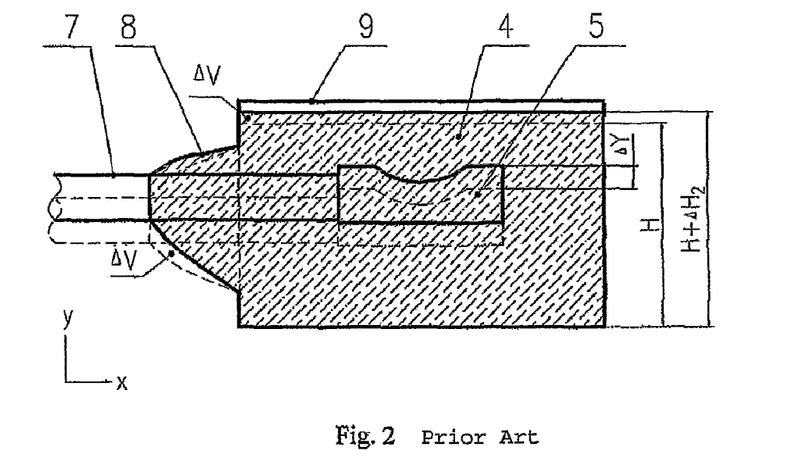
FIG. 2 is a structural diagram of an ultrasonic therapeutic device of prior art. It shows the level changes of couplant liquid when the moving unit drives the ultrasonic therapeutic applicator to move in Y-direction.

In a focused ultrasonic therapeutic system, the ultrasonic waves transmitted from the ultrasonic transducer are eventually focused at the targeted location through the couplant liquid. For an ultrasonic transducer with a fixed focal point, the movement of the focal point is realized by external moving locating mechanism, for example, the mechanical arm 7 shown in FIG. 1 and FIG. 2. As shown in FIG. 1 and FIG. 2, the ultrasonic therapeutic applicator 5 and some part of the mechanical arm 7 are located in the box 9 that contains couplant liquid 4. The mechanical arm 7 is seal-connected with the box 9 through a flexible joining unit 8. During treatment, when the mechanical arm 7 drives the focal point of ultrasonic therapeutic device to move within the target area, the level of couplant liquid in the box will vary accordingly. As shown in FIG. 1, when the ultrasonic therapeutic applicator 5 moves $\Delta X$ along the positive direction of X-axis, the level of couplant liquid in the box will change from H to $H+\Delta H_1$. As shown in FIG. 2, when the ultrasonic therapeutic applicator 5 moves $\Delta Y$ along the positive direction of Y-axis, the level of couplant liquid in the box will change from H to $H+\Delta H_2$.

In the prior art, the flexible joining unit 8 sometimes adopts flexible telescopic sleeve. If the shape of telescopic sleeve is selected appropriately, when the ultrasonic therapeutic applicator moves in Y-direction, $\Delta H_2=0$ and the liquid level keeps unchanged; but when the ultrasonic therapeutic applicator moves in X-direction and when $\Delta X \neq 0$, $\Delta H_1 \neq 0$ and the liquid level varies.

When the imaging device is introduced with the ultrasonic therapeutic system, especially an MRI (Magnetic Resonance Imaging) apparatus, the level changes of couplant liquid will influence the imaging results of MRI and accordingly the diagnostic effect of MRI is influenced.

Therefore, it is very important for an ultrasonic therapeutic system guided by MRI to keep the level of couplant liquid unchanged.

SUMMARY OF THE INVENTION

Aiming at the disadvantages of ultrasonic therapeutic system in the prior art as mentioned above, the present invention is to provide an ultrasonic therapeutic device and an ultrasonic therapeutic system of using the same, which can keep the level of couplant liquid stable when the ultrasonic therapeutic applicator moves. Thus, during treatment, the ultrasonic therapeutic system guided by an imaging device keeps the level of couplant liquid stable when the ultrasonic therapeutic applicator moves. Accordingly, the interference to imaging results of the imaging device due to changes of the liquid level can be reduced effectively, and the diagnostic accuracy of the imaging device and the therapeutic effects of the ultrasonic therapeutic device can be improved.

The technical solution for the problems proposed by the present invention is as follows: the ultrasonic therapeutic device comprises an ultrasonic therapeutic applicator that includes an ultrasonic transducer, a box for containing the ultrasonic therapeutic applicator and couplant liquid, and a moving unit that extends through the wall of box and is connected to the ultrasonic therapeutic applicator. Wherein, compensating units, which will make the level of couplant liquid in the box unchanged when the moving unit drives the ultrasonic therapeutic applicator to move, are arranged on the box.

Said compensating units can be arranged at opposing sides of the box and incorporate with the box. The moving unit extends through both of the compensating units and the ultrasonic therapeutic applicator is located between the two compensating units.

Preferably, said compensating units can be two flexible telescopic sleeves with the same shape and size.

During ultrasonic treatment, the compensating unit adopts flexible material so that it can move with the movement of moving unit when the ultrasonic transducer moves under the control of moving unit.

Said moving unit may be a mechanical arm. The ultrasonic therapeutic applicator is located in the middle of the mechanical arm. Two flexible telescopic sleeves as compensating units are located at opposing sides of ultrasonic therapeutic applicator and are seal-connected with the mechanical arm.

More preferably, said two flexible telescopic sleeves are symmetrically arranged at opposing sides of the box and the mechanical arm extends through the two flexible telescopic sleeves.

The shape of the telescopic sleeve can be any shape that can compensate the liquid volume. In the present invention, in order to make an easy manufacture of the telescopic sleeve and to make use of its symmetrical arrangement more effectively, preferably the telescopic sleeve can be truncated-cone-shaped or prismoid-shaped.

Said ultrasonic therapeutic applicator may be the ultrasonic transducer with a variable focal length or a fixed one. For an ultrasonic transducer with a variable focal length, its focal point may be changed by changing the driving signals or by controlling the moving unit or by both of them. For an ultrasonic transducer with a fixed focal length, its focal point can be changed only by controlling the moving unit. Therefore, the ultrasonic therapeutic applicator with an ultrasonic transducer having a fixed focal length is especially suitable to be used in the present invention.

An ultrasonic therapeutic system of using the ultrasonic therapeutic device as mentioned above guided by an imaging device is available.

In said ultrasonic therapeutic system guided by an imaging device, the imaging device can be B-mode scanner, CT, MRI and etc. When the B-mode scanner and CT are used to guide the ultrasonic therapeutic system for treatment, the changes on liquid level do not influence their imaging obviously; therefore, the present invention is especially applicable to MRI-guided ultrasonic therapeutic system.

For the ultrasonic therapeutic system guided by an imaging device of the present invention, when the ultrasonic therapy applicator moves during treatment, the level of couplant liquid keeps stable due to the use of compensating units. Thus, the phenomenon of level changing of couplant liquid caused by the movement of the ultrasonic therapeutic applicator driven by moving unit in the prior art can be eliminated. A stable liquid level in the box can be ensured and accordingly the interference to imaging results of the imaging device due to liquid level changes can be reduced effectively and the diagnostic accuracy of the imaging device can be improved.

BRIEF DESCRIPTION OF THE DRAWINGS

FIG. 6b is a side view of FIG. 6a.

FIG. 9b is a side view of FIG. 9a.

Wherein:

Broken lines indicate the original position of the subject before it moves.

1, 7—Mechanical arm 2—First compensating unit 3, 9—Box 4—Couplant liquid 5—Ultrasonic therapeutic applicator 6—Second compensating unit 8—Flexible joining unit

DETAILED DESCRIPTION OF PREFERRED EMBODIMENTS

The present invention will be further explained below in detail with reference to the preferred embodiments and accompanying drawings.

Figure 3:
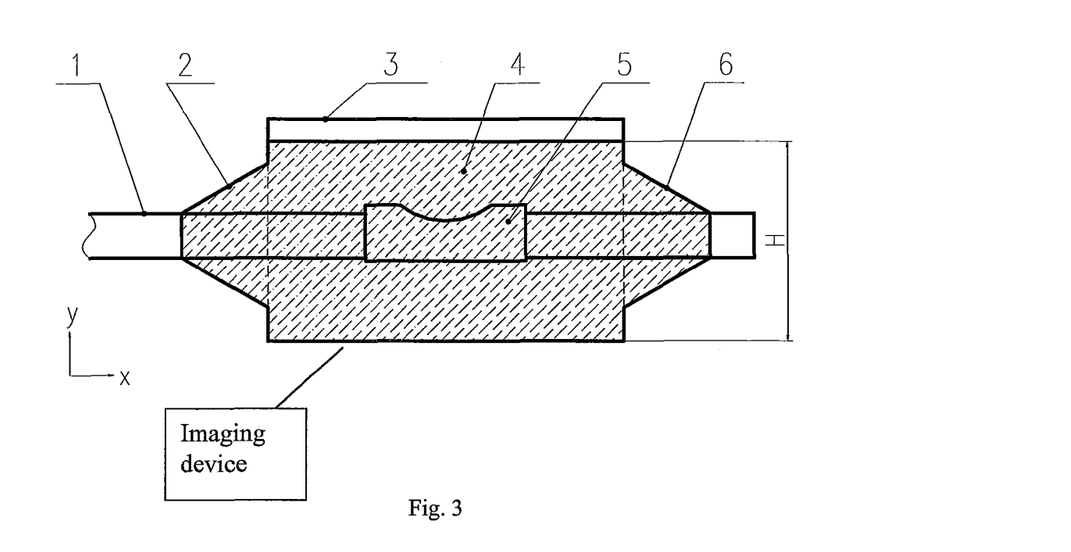
FIG. 3 is a structural diagram of an ultrasonic therapeutic device of the present invention.
Figure 4:
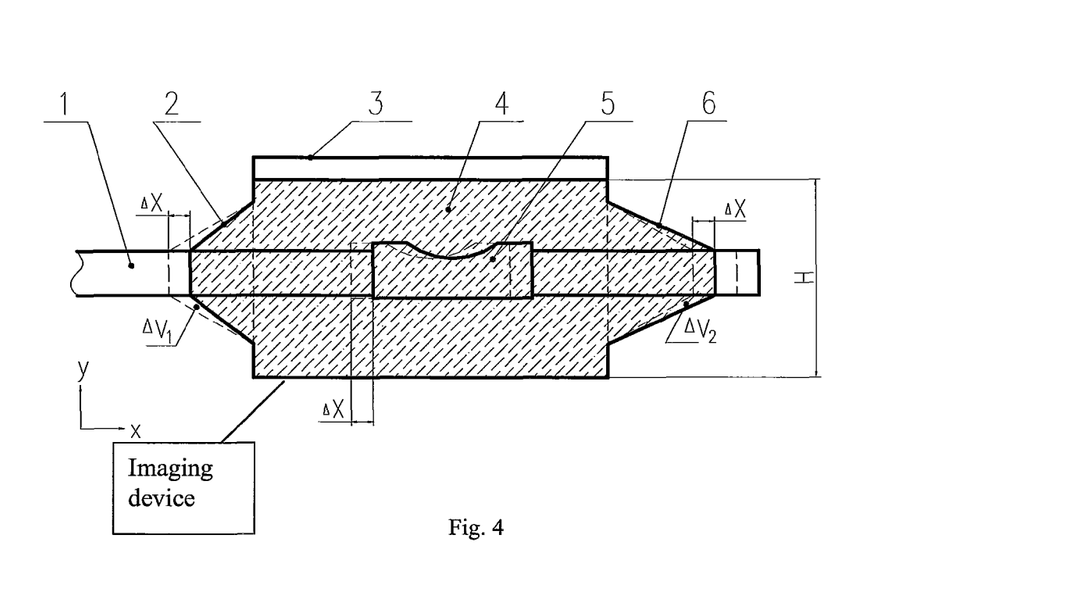
FIG. 4 is a structural diagram of an ultrasonic therapeutic device of the present invention. It shows the level changes of couplant liquid when the moving unit drives the ultrasonic therapeutic applicator to move in X-direction.
Figure 5:
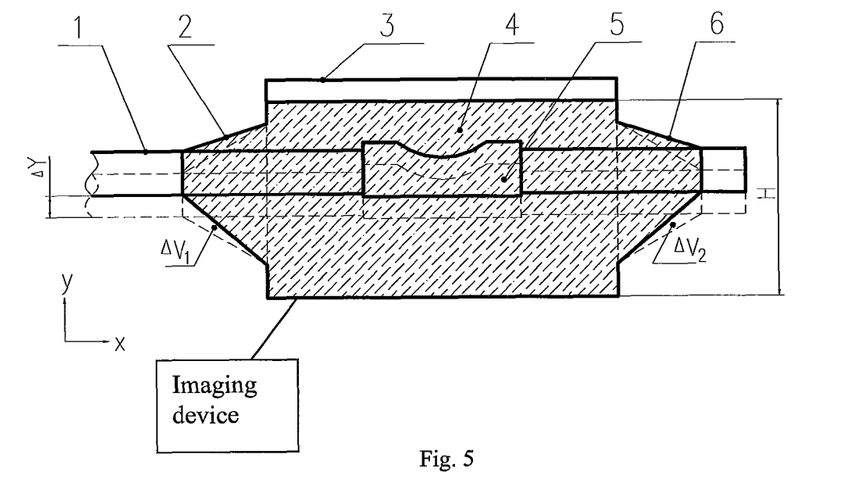
FIG. 5 is a structural diagram of an ultrasonic therapeutic device of the present invention. It shows the level changes of couplant liquid when the moving unit drives the ultrasonic therapeutic applicator to move in Y-direction.

As shown in FIG. 3, FIG. 4 and FIG. 5, the ultrasonic therapeutic system guided by an imaging device consists of an imaging device for imaging the target and an ultrasonic therapeutic device. Said ultrasonic therapeutic device comprises an ultrasonic therapeutic applicator 5 that includes an ultrasonic transducer, a box 3, and a moving unit that is connected to the ultrasonic therapeutic applicator 5 and controls its movement, i.e. mechanical arm 1.

The ultrasonic therapeutic applicator 5 is placed in the box 3 that is full of couplant liquid. The mechanical arm 1 that drives ultrasonic therapeutic applicator 5 to move, extends through the wall of the box and is connected to the ultrasonic therapeutic applicator 5. The compensating units are arranged on the box 3 and make the level of couplant liquid in the box 3 unchanged when the mechanical arm 7 drives the ultrasonic therapeutic applicator 5 to move.

Said compensating units are the first compensating unit 2 and the second compensating unit 6, which are arranged symmetrically at opposing sides of the box 3 and incorporate with the box 3. The two symmetrical compensating units have the same shape and size. The mechanical arm 1 extends horizontally through the two symmetrical compensating units; the ultrasonic therapeutic applicator 5 on the mechanical arm 1 is located between the two compensating units. The two compensating units are sealed and fixed with the mechanical arm 1 at one end and are sealed and fixed with the box 3 at the other end. The compensating units adopt flexible telescopic sleeves, which are made from flexible material. At the connection points of two flexible telescopic sleeves, the mechanical arm 1 has a suitable shape corresponding to the connection ends of flexible telescopic sleeves. Two flexible telescopic sleeves have certain capability of repeated deformation when driven by the mechanical arm 1. For example, when the mechanical arm 1 moves in X-direction, two flexible telescopic sleeves correspondingly elongate or shorten the same length in X-direction; when the mechanical arm 1 moves in Y-direction and Z-direction, two flexible telescopic sleeves deform correspondingly.

During treatment, the mechanical arm 1 drives the ultrasonic therapeutic applicator 5 to move and accordingly its focal point moves. The ultrasonic waves transmitted from the ultrasonic therapeutic applicator 5 go through the couplant liquid 4 and then are focused at the target (not illustrated in figures.). The focal point of the ultrasonic therapeutic applicator 5 can move in X, Y, Z-directions to meet the requirements for the three-dimensional entity of the target to be treated. The compensating units move when the mechanical arm 1 moves and can deform in X, Y, Z-directions.

When the focal point of the ultrasonic transducer is required to move in X-direction, the mechanical arm 1 drives the ultrasonic therapeutic applicator 5 to move in X-direction. As shown in FIG. 4, when the mechanical arm 1 moves ΔX toward +X-direction, it drives the ultrasonic therapeutic applicator 5 to move ΔX and meanwhile the first compensating unit 2 shortens ΔX and the second compensating unit 6 elongates ΔX. The volume change in the first compensating unit 2 is $\Delta V_1$ and the volume change in the second compensating unit 6 is $\Delta V_2$. A certain structural shape for the first compensating unit 2 and the second compensating unit 6 can be selected so that the formula $\Delta V_1 + \Delta V_2 = 0$ becomes possible. Therefore, when the ultrasonic therapeutic applicator 5 moves in X-direction, the sum of volumes of the box 3 and the two compensating units is not changed and accordingly the level of couplant liquid in the box keeps unchanged before and after the mechanical arm moves.

When the focal point of the ultrasonic transducer is required to move in Y-direction, the mechanical arm 1 drives the ultrasonic therapeutic applicator 5 to move in Y-direction. As shown in FIG. 5, when the mechanical arm 1 moves ΔY toward +Y-direction, it drives the ultrasonic therapeutic applicator 5 to move ΔY and meanwhile the first compensating unit 2 and the second compensating unit 6 move ΔY in Y-direction. The volume change in the first compensating unit 2 is $\Delta V_1$ and the volume change in the second compensating unit 6 is $\Delta V_2$. A certain structural shape for the first compensating unit 2 and the second compensating unit 6 can be selected so that the formula $\Delta V_1 + \Delta V_2 = 0$ becomes possible. Therefore, when the ultrasonic therapeutic applicator 5 moves in Y-direction, the sum of volumes of the box 3 and the two compensating units is not changed and accordingly the level of couplant liquid in the box keeps unchanged before and after the mechanical arm moves.

When the focal point of the ultrasonic transducer is required to move in Z-direction, the conditions of movement can be analyzed with reference to the movement in Y-direction and it will not be repeated here.

In the following two embodiments, only the shape changes of the compensating units are described and other structures are the same as mentioned above. Here the MRI apparatus is selected as the imaging device and the ultrasonic transducer in the ultrasonic therapeutic applicator 5 adopts an ultrasonic transducer with a fixed focal length.

EMBODIMENT 1

Figure 6A:
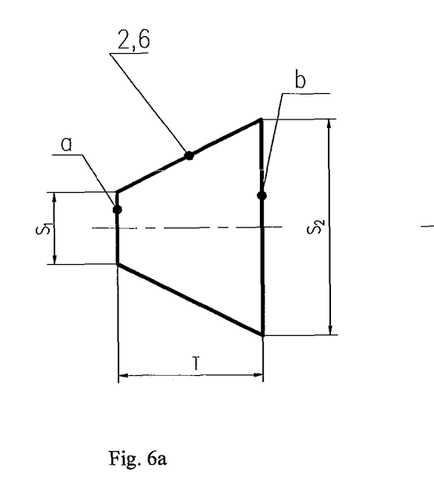
FIG. 6a is a front view of the structure of the truncated-cone-shaped telescopic sleeve under the initial status of the ultrasonic therapeutic device in the embodiment 1 of the present invention.
Figure 6B:
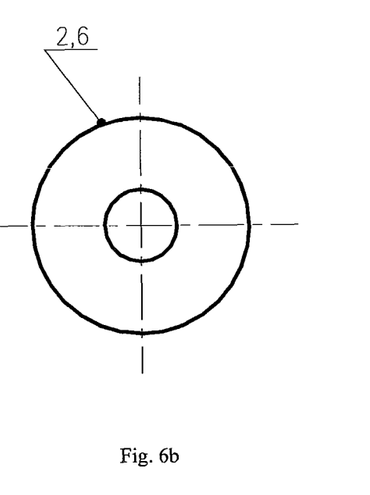

As shown in FIG. 6a and FIG. 6b, in this embodiment, both the first compensating unit 2 and the second compensating unit 6 adopt truncated-cone-shaped flexible telescopic sleeves. The area of the upper surface of truncated-cone (small end "a") is $S_1$ and the area of the lower surface of truncated-cone (big end "b") is $S_2$. The length of the truncated-cone is T when the ultrasonic therapeutic applicator 5 is in static status. The small end "a" is fixed with and connected to the mechanical arm 1 and the big end "b" is fixed with and connected to the box 3.

Figure 7A:
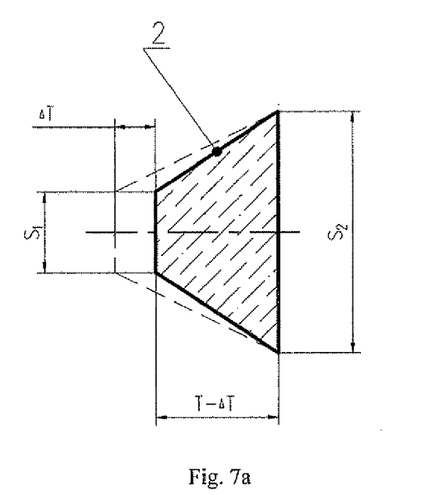
FIG. 7a shows the shape changes of the first compensating unit 2 when the mechanical arm 1 moves in X-direction in the embodiment 1 of the present invention.
Figure 7B:
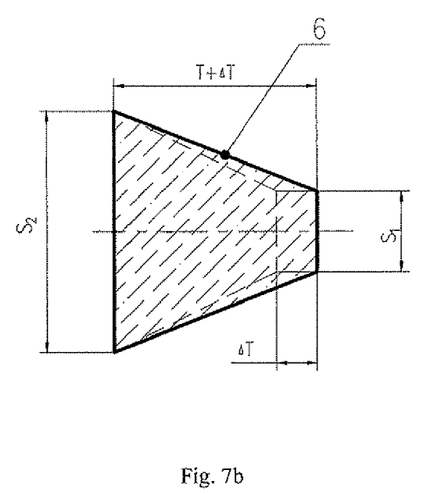
FIG. 7b shows the shape changes of the second compensating unit 6 when the mechanical arm 1 moves in X-direction in the embodiment 1 of the present invention.

Under the control of the mechanical arm 1, when the focal point of the ultrasonic therapeutic applicator 5 moves in X-direction (as shown in FIG. 4), as shown in FIG. 7a and FIG. 7b, V=volume of telescopic sleeve, from geometry we know.

$$V = \frac{1}{3} \times \left(S_1 + \sqrt{S_1 \times S_2} + S_2\right) \times T$$

When the ultrasonic therapeutic applicator 5 moves towards X-direction, $S_1$ is not changed during movement because the small end "a" of the truncated-cone-shaped compensating unit is fixed with the mechanical arm 1 and meanwhile $S_2$ is also not changed because the big end "b" of the truncated-cone-shaped compensating unit is fixed with the box 3.

FIG. 7a shows the shape changes of the first compensating unit 2 as below:

$$\Delta V_1 = \frac{1}{3} \times \left(S_1 + \sqrt{S_1 \times S_2} + S_2\right) \times T - \frac{1}{3} \times \left(S_1 + \sqrt{S_1 \times S_2} + S_2\right) \times (T - \Delta T)$$
$$= \frac{1}{3} \times \left(S_1 + \sqrt{S_1 \times S_2} + S_2\right) \times \Delta T$$

FIG. 7b shows the shape changes of the second compensating unit 6 as below:

$$\Delta V_2 = \frac{1}{3} \times \left(S_1 + \sqrt{S_1 \times S_2} + S_2\right) \times T - \frac{1}{3} \times \left(S_1 + \sqrt{S_1 \times S_2} + S_2\right) \times (T + \Delta T)$$
$$= -\frac{1}{3} \times \left(S_1 + \sqrt{S_1 \times S_2} + S_2\right) \times \Delta T$$

$$\Delta V_1 + \Delta V_2 =$$
$$\frac{1}{3} \times \left(S_1 + \sqrt{S_1 \times S_2} + S_2\right) \times \Delta T - \frac{1}{3} \times \left(S_1 + \sqrt{S_1 \times S_2} + S_2\right) \times \Delta T = 0$$

Therefore, when moving in X-direction, the total volume change of the two compensating units is zero and the level of couplant liquid keeps stable.

Figure 8A:
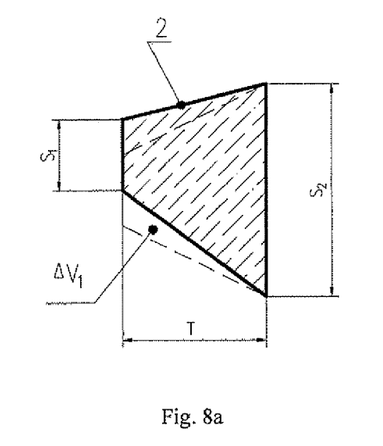
FIG. 8a shows the shape changes of the first compensating unit 2 when the mechanical arm 1 moves in Y-direction in the embodiment 1 of the present invention.

When the focal point of the ultrasonic therapeutic device in FIG. 3 moves towards Y-direction, under the control of the mechanical arm 1, the focal point of the ultrasonic therapeutic applicator 5 moves towards Y-direction (as shown in FIG. 5). The volume change of the first compensating unit 2 is shown in FIG. 8a:

$$\Delta V_1 = \frac{1}{3} \times \left(S_1 + \sqrt{S_1 \times S_2} + S_2\right) \times T - \frac{1}{3} \times \left(S_1 + \sqrt{S_1 \times S_2} + S_2\right) \times T = 0$$

Figure 8B:
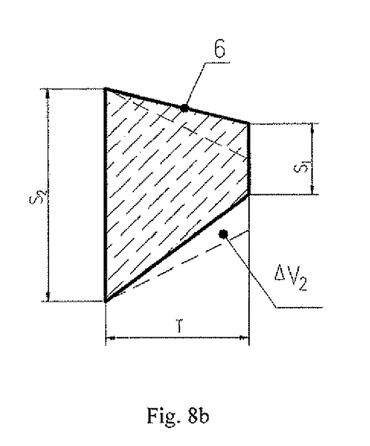
FIG. 8b shows the shape changes of the second compensating unit 6 when the mechanical arm 1 moves in Y-direction in the embodiment 1 of the present invention.

The volume change of the second compensation unit 6 is shown in FIG. 8b:

$$\Delta V_2 = \frac{1}{3} \times \left(S_1 + \sqrt{S_1 \times S_2} + S_2\right) \times T - \frac{1}{3} \times \left(S_1 + \sqrt{S_1 \times S_2} + S_2\right) \times T = 0$$
$$\Delta V_1 + \Delta V_2 = 0$$

Therefore, when moving in Y-direction, the total volume change of the two compensation units is zero and the level of couplant liquid keeps stable.

The conditions of movement when the ultrasonic therapeutic device moves towards Z-direction are the same as when moving towards Y-direction and it will not be repeated here.

From this, it can be seen that in this embodiment, the level of couplant liquid can keep stable surely when the ultrasonic therapeutic applicator 5 moves in X, Y and Z-directions and when the mechanical arm 1 drives the focal point of the ultrasonic therapeutic applicator to move.

EMBODIMENT 2

Figure 9A:
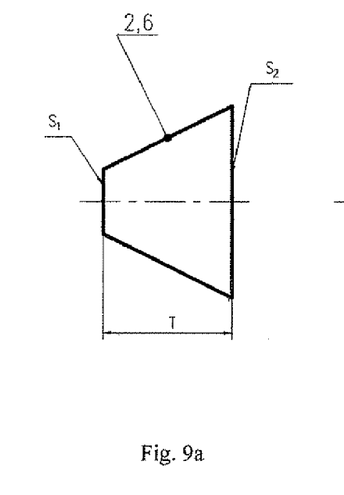
FIG. 9a is a front view of the structure of the prismoid-shaped telescopic sleeve under the initial status of the ultrasonic therapeutic device in the embodiment 2 of the present invention.
Figure 9B:
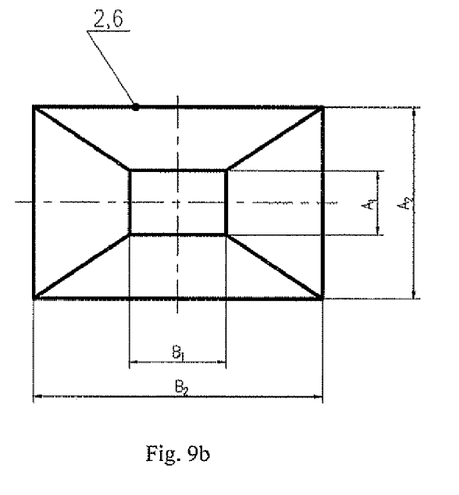

As shown in FIG. 9a and FIG. 9b, in this embodiment, the first compensating unit 2 and the second compensating unit 6 are prismoid-shaped flexible telescopic sleeves. The length and width of its upper surface is $B_1$ and $A_1$, and its area is $S_1$. The length and width of its lower surface is $B_2$ and $A_2$, and its area is $S_2$. The height of the prismoid is T. The other structures are the same as those in embodiment 1.

Volume of prismoid:

$$V_{prismoid} = \frac{1}{3} \times \left(S_1 + \sqrt{S_1 \times S_2} + S_2\right) \times T$$

Figure 10A:
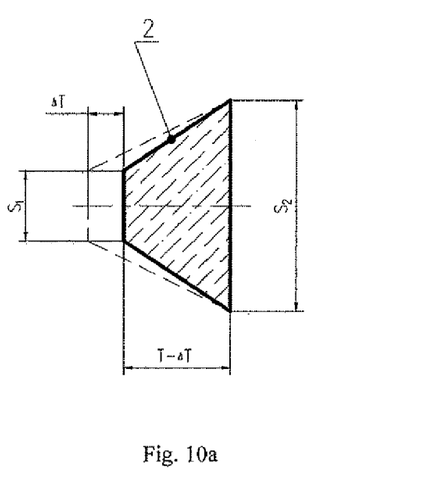
FIG. 10a shows the shape changes of the first compensating unit 2 when the mechanical arm 1 moves in X-direction in the embodiment 2 of the present invention.

When the ultrasonic therapeutic applicator 5 in FIG. 4 moves towards X-direction, as shown in FIG. 10a, the height of the first compensating unit 2 is changed from T to T−ΔT, but S1 and S2 are not changed during movement. The volume change of the first compensating unit 2 after movement is as below:

$$\Delta V_1 = \frac{1}{3} \times \left(S_1 + \sqrt{S_1 \times S_2} + S_2\right) \times T -$$

$$\frac{1}{3} \times \left(S_1 + \sqrt{S_1 \times S_2} + S_2\right) \times (T - \Delta T)$$

$$= \frac{1}{3} \times \left(S_1 + \sqrt{S_1 \times S_2} + S_2\right) \times \Delta T$$

Figure 10B:
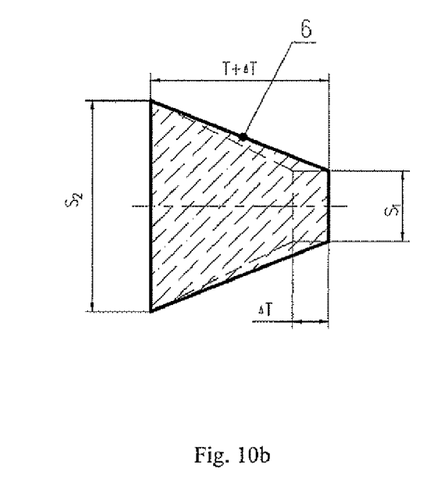
FIG. 10b shows the shape changes of the second compensating unit 6 when the mechanical arm 1 moves in X-direction in the embodiment 2 of the present invention.

As shown in FIG. 10b, the height of the second compensating unit 6 is changed from T to T+ΔT, but S1 and S2 are not changed during movement. The volume change of the second compensating unit 6 after movement is as below:

$$\Delta V_2 = \frac{1}{3} \times \left(S_1 + \sqrt{S_1 \times S_2} + S_2\right) \times T -$$

$$\frac{1}{3} \times \left(S_1 + \sqrt{S_1 \times S_2} + S_2\right) \times (T + \Delta T)$$

$$= -\frac{1}{3} \times \left(S_1 + \sqrt{S_1 \times S_2} + S_2\right) \times \Delta T$$

$\Delta V_1 + \Delta V_2 =$ $$\frac{1}{3} \times \left(S_1 + \sqrt{S_1 \times S_2} + S_2\right) \times \Delta T - \frac{1}{3} \times \left(S_1 + \sqrt{S_1 \times S_2} + S_2\right) \times \Delta T = 0$$

Therefore, when moving in X-direction, the total volume change of the two compensating units is zero and the level of couplant liquid keeps stable.

Figure 11A:
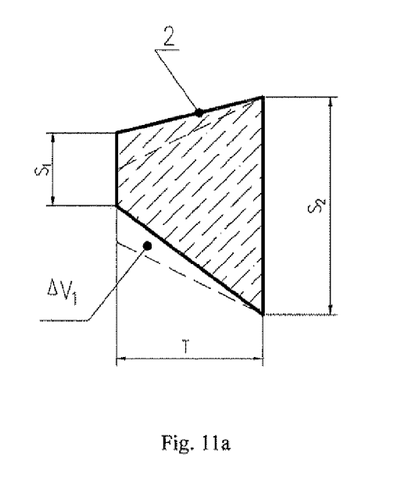
FIG. 11a shows the shape changes of the first compensating unit 2 when the mechanical arm 1 moves in Y-direction in the embodiment 2 of the present invention.

When the focal point of the ultrasonic therapeutic applicator 5 in FIG. 5 moves towards Y-direction, the volume change of the first compensating unit 2 is shown in FIG. 11a:

$$\Delta V_1 = \frac{1}{3} \times \left(S_1 + \sqrt{S_1 \times S_2} + S_2\right) \times T - \frac{1}{3} \times \left(S_1 + \sqrt{S_1 \times S_2} + S_2\right) \times T = 0$$

Figure 11B:
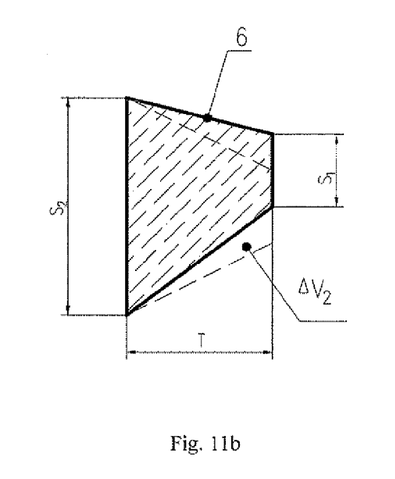
FIG. 11b shows the shape changes of the second compensating unit 6 when the mechanical arm 1 moves in Y-direction in the embodiment 2 of the present invention.

The volume change of the second compensating unit 6 is shown in FIG. 11b:

$$\Delta V_2 = \frac{1}{3} \times \left(S_1 + \sqrt{S_1 \times S_2} + S_2\right) \times T - \frac{1}{3} \times \left(S_1 + \sqrt{S_1 \times S_2} + S_2\right) \times T = 0$$

$$\Delta V_1 + \Delta V_2 = 0$$

Therefore, when moving in Y-direction, the total volume change of the two compensating units is zero and the level of couplant liquid keeps stable.

From this, we can conclude that the sum of volumes of the two compensating units before and after movement keeps unchanged and the level of couplant liquid will keep the original level.

The conditions of movement when the ultrasonic therapeutic device moving towards Z-direction are the same as when moving towards Y-direction and it will not be repeated here.

From the embodiment 1 and embodiment 2, it can be seen that two flexible telescopic sleeves arranged symmetrically at opposing sides of the box 3 and sealed and fixed with the mechanical arm 1 are provided here, so that the level of couplant liquid can keep stable surely when the mechanical arm 1 moves in X, Y and Z-directions, and accordingly the interference to MRI can be minimized to the utmost and the diagnostic accuracy of MRI apparatus is improved.

The invention claimed is:

1. An ultrasonic therapeutic device comprising an ultrasonic therapeutic applicator that includes an ultrasonic transducer, a box containing the ultrasonic therapeutic applicator and couplant liquid, and a moving unit for the ultrasonic therapeutic applicator that extends through a wall of the box and is connected to the ultrasonic therapeutic applicator and two compensating units, wherein said two compensating units are arranged at opposing sides of the box and are incorporated with the box; and wherein the moving unit extends through both of the compensating units and the ultrasonic therapeutic applicator is located between the compensating units; said compensating units being shaped to make the total volume change of the compensating units be zero when the moving unit drives the ultrasonic therapeutic applicator to move, so that the level of the couplant liquid in the box remains unchanged.

2. The ultrasonic therapeutic device of claim 1, wherein each of said compensating units comprises a flexible telescopic sleeve.

3. The ultrasonic therapeutic device of claim 2, wherein said flexible telescopic sleeves initially have a same shape and size with respect to each other.

4. The ultrasonic therapeutic device of claim 3, wherein said moving unit is a mechanical arm, and the ultrasonic therapeutic applicator is located at a central portion of the mechanical arm; and the flexible telescopic sleeves are located at opposing sides of the ultrasonic therapeutic applicator and are seal-connected with the mechanical arm.

5. The ultrasonic therapeutic device of claim 4, wherein said flexible telescopic sleeves are arranged at opposing sides of the box symmetrically and the mechanical arm extends through the flexible telescopic sleeves.

6. The ultrasonic therapeutic device of claim 5, wherein said flexible telescopic sleeves are truncated-cone-shaped or prismoid-shaped.

7. An ultrasonic therapeutic system comprising an imaging device and the ultrasonic therapeutic device, as claimed in any one of claims 1-6, wherein the ultrasonic therapeutic device is guided by the imaging device.

8. The ultrasonic therapeutic system of claim 7, wherein said imaging device is an MRI apparatus.

* * * * *